United States Patent

Weiss et al.

[11] 4,024,639
[45] May 24, 1977

[54] BONE IMPLANTS AND METHOD FOR INSERTING THE SAME

[75] Inventors: Fredric M. Weiss, Suffern; David P. Malkin, Bluepoint, both of N.Y.; James Pugh, Edgewater, N.J.; Charles Weiss, Newton, Mass.

[73] Assignee: End-Dent, Inc., Suffern, N.Y.

[22] Filed: Feb. 25, 1975

[21] Appl. No.: 552,789

[52] U.S. Cl. .............................................. 32/10 A
[51] Int. Cl.² ......................................... A61C 13/00
[58] Field of Search .................. 32/10 A; 128/92 C

[56] References Cited

UNITED STATES PATENTS

| 581,335 | 4/1897 | Carr | 32/10 A |
|---|---|---|---|
| 3,085,334 | 4/1963 | Bischof et al. | 32/10 A |
| 3,589,011 | 6/1971 | Sneer | 32/10 A |
| 3,672,058 | 6/1972 | Nikoghossian | 32/10 A |
| 3,729,825 | 5/1973 | Linkow et al. | 32/10 A |
| 3,808,606 | 5/1974 | Tronzo | 32/10 A X |
| 3,827,145 | 8/1974 | Richards | 32/10 A |
| 3,919,773 | 11/1975 | Freeman | 128/92 C X |

FOREIGN PATENTS OR APPLICATIONS

| 1,278,967 | 6/1972 | United Kingdom | 32/10 A |
|---|---|---|---|
| 1,306,027 | 2/1973 | United Kingdom | 128/92 C |

*Primary Examiner*—Robert Peshock
*Attorney, Agent, or Firm*—Lee C. Robinson, Jr.

[57] ABSTRACT

A dental implant which is imbedded within a body of acrylic material in a channel formed in the jawbone such that no portion of the implant comes in contact with the bone. The implant includes one or more projecting pins for supporting an artificial tooth and a series of lateral projections which extend into the acrylic material to hold the implant in place.

11 Claims, 5 Drawing Figures

BONE IMPLANTS AND METHOD FOR INSERTING THE SAME

BACKGROUND OF THE INVENTION

This invention relates to implant devices and more particularly to a bone implant and a method for inserting the implant into a cavity in the bone.

The present invention, while of general medical application for humans and other vertebrates, is particularly well suited for use in the field of dentistry to provide support for artificial teeth. In cases in which there are natural abutment teeth of sufficient strength and rigidity, the artificial teeth may be supported by conventional bridgework. However, this is not always the case, and it then becomes necessary to surgically implant a support member in the jawbone in order to provide a firm base on which to mount the artificial tooth.

The most common implants in present usage are fabricated from stainless steal or other metallic material. However, the metal implants utilized heretofore for dental purposes, and also in the fields of orthopedics and neurosurgery, for example, frequently have exhibited a corrosive action in the presence of living bone with the result that an electrolytic current or other adverse reaction was created with serious deleterious effect.

To alleviate this problem, various proposals have been made to form the implant from acrylic polymers and other inert materials. One of the difficulties encountered with such previous proposals was that the materials often did not have the necessary structural properties to provide adequate support. In addition, and this has been of special moment for implants made from acrylics such as methylmethacrylate resins, difficulties were encountered in maintaining the implant in its proper position for an extended period of time under the hard usage encountered in the mouth.

SUMMARY

One general object of this invention, therefore, is to provide a new and improved implant and a method for inserting the implant into a cavity in the supporting bone.

More specifically, it is an object of this invention to provide such an implant and method wherein the implant is biologically acceptable to the adjacent bone structure and yet exhibits sufficient strength to firmly support an artificial tooth.

Another object of this invention is to provide an implant of the character indicated which is mounted in rigid relationship with the bone and remains in position over an extended period of time.

A further object of the invention is to provide a bone implant which is economical to manufacture and install and is thoroughly reliable in usage.

In one illustrative embodiment of the invention there is provided a dental implant which includes an elongate support member of a cobalt-chromium alloy or other comparatively high-strength material. The support member advantageously is of rectangular cross-section and has a pair of generally vertical opposed surfaces. To insert the support member in the mouth, a surgical incision is made in the tissue layer overlying the alveolar portion of the jawbone to provide a flap of tissue and expose a portion of the bone. An elongate cavity or channel is formed in the exposed portion of the bone through the use of a dental burr or other appropriate tool, and the support member is imbedded in the cavity. The support member includes one or more upstanding pins which protrude from the cavity for connection to an artificial tooth.

In accordance with one feature of the invention, in certain particularly important embodiments, a body of nontoxic acrylic resin is disposed within the cavity around the support member and is arranged to prevent all contact between the support member and the bone structure. The support member is imbedded in the resinous material with the material disposed between the member and the adjacent bone. The arrangement is such that any corrosive action between the support member and the bone is substantially reduced while at the same time providing ample strength and rigidity to firmly support the artificial tooth.

In accordance with another feature of several advantageous embodiments of the invention, the support member includes a plurality of integrally formed lateral projections which extend in a transverse direction from each of the members' opposed surfaces. The lateral projections are imbedded in the resinous material to hold the member in place and yet avoid all contact between the member and the bone structure. With this arrangement, the member is maintained in rigid relationship with the bone and remains in position over an extended period of time.

The present invention, as well as further objects and features thereof, will be more fully understood from the following description of a preferred embodiment, when read with reference to the accompanying drawings.

DESCRIPTION OF A PREFERRED EMBODIMENT

Figure 1:
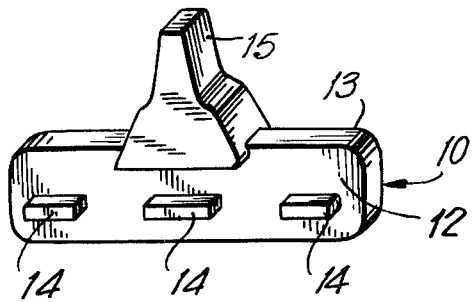
FIG. 1 is a perspective view of a dental implant in accordance with an illustrative embodiment of the invention.
Figure 2:
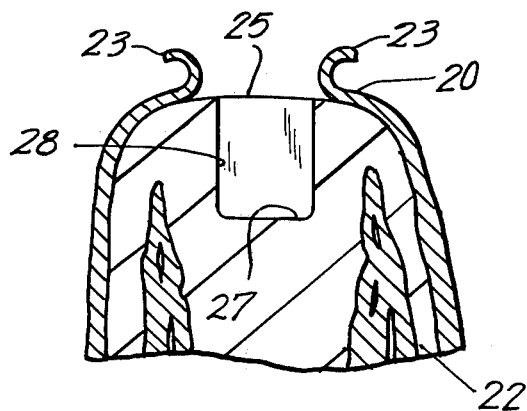
FIGS. 2 through 5 are successive schematic sectional view of the lower jawbone illustrating the various sequential steps in the insertion of the implant into the bone structure.
Figure 4:
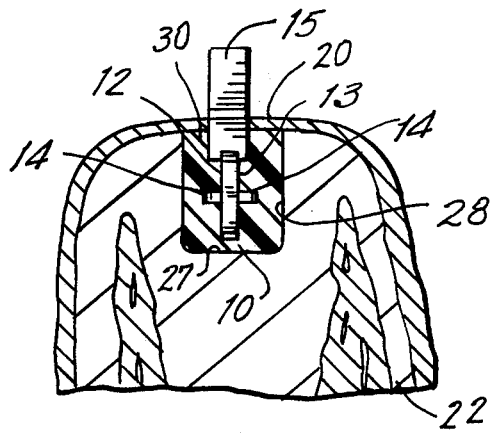
Figure 5:
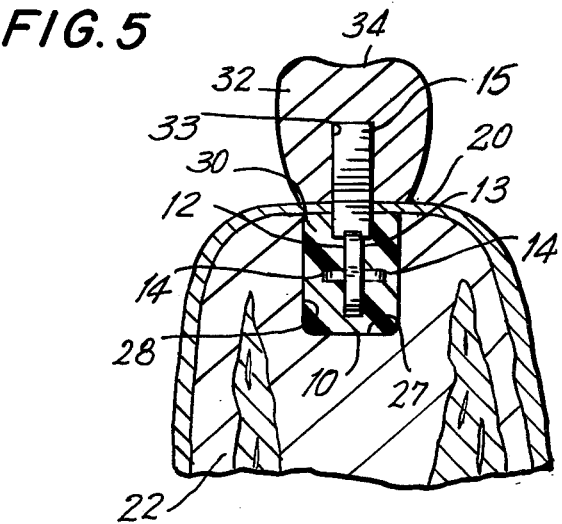

Referring to FIG. 1 of the drawings, there is shown a dental implant in the form of an elongate support member indicated generally at 10. The support member 10 advantageously is fabricated from a cobalt-chromium alloy, although other metallic materials having the necessary strength and rigidity also may be employed with good effect. The member 10 is of rectangular cross-section and is provided with a pair of opposed flat surfaces 12 and 13 which, as best illustrated in FIGS. 4 and 5, extend in parallel vertical planes.

Protruding laterally from the support member 10 are six integrally formed projections 14. Three of the projections 14 extend in a transverse direction from each of the opposed surfaced 12 and 13, and the projections are arranged in oppositely extending pairs on the two sides of the support member.

An upstanding pin 15 is disposed on the upper surface of the support member 10 in rigid relationship therewith. This pin, which by itself is conventional, is of generally rectangular cross-section and is provided with a distinct taper to accommodate a mating aperture in an artificial tooth or other structure to be supported. Although the support member 10 illustrated in the drawings has only one such pin, it of course will be understood that the number of pins on a particular support member will depend on the type, size and number of artificial teeth or other supported structure.

FIGS. 2 through 5 are illustrative of the successive steps employed in inserting the support member 10 into the bone structure. Referring in FIG. 2, a surgical incision is made in the gingival membrane 20 overlying the jawbone 22 to provide a pair of tissue flaps 23. These flaps are turned back in the manner illustrated to expose the alveolar crest 25 of the bone 22.

though the use of a fissure burr or other appropriate tool, an elongate cavity or channel 27 is formed in the jawbone 22. The channel 27 is of rectangular cross-section and is of a size such that the overall dimensions of the support member 10 are respectively less than the corresponding dimensions of the channel. The channel is provided with an interior surface 28 which generally conforms to the shape of the support member.

Figure 3:
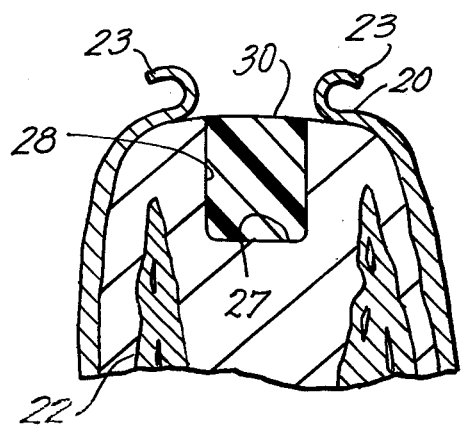

As best shown in FIG. 3, a body of nontoxic acrylic material 30 is then inserted within the cavity 27 such that the material covers substantially the entire interior surface 28 of the cavity. The material 30 is not used as an adhesive but rather as a filler to provide an inert resinous mass within the cavity which is biologically acceptable to the adjacent bone structure. Although a wide variety of materials may be employed for this purpose, particularly advantageous results are obtained through the use of a sterile, cold cure polymethylmethacrylate polymer having various components catalysts, and inhibitors such as polymethylmethacrylate, methylmethacrylate, monomer, polystyrene, barium sulfate, benzoyl peroxide, hydroquinone and di-methyl-p-toluidine. Representative acrylic materials which may be employed with good effect include those commercially available under the trademarks SIMPLEX, CMW, KAOLODENT and DUZALL.

With the body of acrylic material 30 in place within the cavity 27, the support member 10 is imbedded in the material such that no portion of the support member contacts the bone structure 22. As best illustrated in FIG. 4, the material 30 is disposed around the support member 10 and serves to prevent all contact between the support member and the bone. The support member is held in place by the lateral projections 14 in spaced relationship with the interior surface 28 of the cavity 27, and the projections serve to prevent upward or downward movement of the support member, as viewed in FIG. 4, with respect to the bone.

The excess acrylic material 30 is then scraped away or otherwise removed. It is important that none of the material extend above the cavity 27, and care must be taken to insure that the upper surface of the material is in substantially coplanar relationship with the alveolar crest 25. The tissue flaps 23 are closed over the cavity 27 in some cases are sutured together depending upon the size of the incision.

Upon the completion of the installation, the pin 15 protrudes above the gum line in position to receive an artificial tooth 32. As illustrated in FIG. 5, the tooth 32 illustratively may comprise a molar crown and includes a suitable recess 33 in the surface opposite the ocllusal or bite surface 34 to accommodate the pin 15. The tooth 32 is cemented on the pin 15 in the usual way.

In the illustrated embodiment the support member 10 extends in a longitudinal direction and is of generally rectangular cross-section. In other advantageous arrangements the support member may be of varying shapes depending upon the particular type of channel or cavity within which it is to be inserted. In some cases, for example, the support member is of arcuate configuration and is provided with a correspondingly shaped channel so that one or both ends of the support member extend more deeply into the channel than the center portion of the member.

The terms and expressions which have been empolyed are used as terms of description and not of limitation, and there is no intention in the use of such terms and expressions of excluding any equivalents of the features shown and described, or portions thereof, it being recognized that various modifications are possible within the scope of the invention claimed.

What is claimed is:

1. A dental implant for insertion into a cavity in bone structure, the implant comprising, in combination:

a support member having a pair of opposed surfaces, the support member including a plurality of generally planar lateral projections extending in a transverse direction from said surfaces, the overall dimensions of the support member being respectively less than the corresponding dimensions of the cavity;

at least one pin means in rigid relationship with the support member and being of a length sufficient to protrude from the cavity, the lateral projections on said support member lying in a plane which is perpendicular to the axis of the pin means and which is transverse of the plane in which said axis of the pin means lies, whereby the plane of said projections intersects said axis of the pin means at a right angle;

and a body of nontoxic filler material adapted to be disposed within the cavity around the support member for permanently preventing all contact between the support member and the bone structure.

2. An implant as defined in claim 1, in which the support member is of metallic material and the filler material comprises an acrylic resin.

3. A dental implant for insertion into a cavity in bone structure, the bone implant comprising, in combination:

a support member having a pair of opposed surfaces, the support member including a plurality of integrally formed generally planar lateral projections extending in a transverse direction from each of said surfaces, the overall dimensions of the support member being respectively less than the corresponding dimensions of the cavity; and at least one pin means in rigid relationship with the support member and being of a length sufficient to protrude from the cavity, the lateral projections on said support member lying in a plane which is perpendicular to the axis of the pin means and which is transverse of the plane in which said axis of the pin means lies, whereby the plane of said projections intersects said axis of the pin means at a right angle.

4. A dental implant for insertion into a cavity in bone structure, the implant comprising, in combination:

an elongate cobalt-chromium alloy support member having a rectangular cross-section and a pair of opposed surfaces, the support member including a plurality of integrally formed generally planar lateral projections extending in a transverse direction from each of said surfaces, the overall dimensions of the support member being respectively less than the corresponding dimensions of the cavity; and at least one pin means in rigid relationship with the support member and being of a length sufficient to protrude from the cavity, the lateral projections on said support member lying in a plane which is perpendicular to the axis of the pin means and which is transverse of the plane in which said axis of the pin means lies, whereby the plane of said projections intersects said axis of the pin means at a right angle.

5. A dental implant for insertion into a cavity in bone structure, the implant comprising, in combination:

an elongate stainless steel support member having a rectangular cross-section and a pair of opposed surfaces, the support member including a plurality of integrally formed generally planar lateral projections extending in a transverse direction from each of said surfaces, the overall dimensions of the support member being respectively less than the corresponding dimensions of the cavity;

at least one pin means in rigid relationship with the support member and being of a length sufficient to protrude from the cavity, the lateral projections on said support member being arranged in oppositely disposed pairs in a single plane which is perpendicular to the axis of the pin means and which is transverse of the plane in which said axis of the pin means lies, whereby the plane of said projections intersects said axis of the pin means at a right angle; and a body of nontoxic acrylic resin adapted to the disposed within the cavity around the support member for permanently preventing all contact between the support member and the bone structure.

6. An implant as defined in claim 5, in which the body of acrylic resin comprises polymethylmethacrylate.

7. A method of inserting a dental implant into bone structure, comprising the steps of:

incising a tissue layer overlying the bone structure to provide a flap of tissue and expose a portion of said structure;

forming a cavity in the exposed portion of the bone structure;

applying a body of nontoxic filler material to substantially the entire interior surface of the cavity;

thereafter imbedding a support member in the filler material in said cavity such that no portion of the support member contacts the bone structure; and 8. A method for inserting a dental implant into bone structure, comprising the steps of:

incising a tissue layer overlying the bone structure to provide a flap of tissue and expose a portion of said structure;

forming a cavity in the exposed portion of the bone structure;

applying a body of nontoxic filler material to substantially the entire interior surface of the cavity;

thereafter imbedding a support member in the filler material in said cavity such that no portion of the support member contacts the bone structure;

holding the support member in spaced relationship with the interior surface of the cavity; and closing the tissue flap over said cavity.

9. A method for inserting a dental implant into bone structure, comprising the steps of:

incising a tissue layer overlying the bone structure to provide a flap of tissue and expose a portion of said structure;

forming a cavity in the exposed portion of the bone structure;

applying a body of nontoxic filler material to substantially the entire interior surface of the cavity, to substantially fill the cavity;

thereafter imbedding a support member in the filler material in said cavity such that no portion of the support member contacts the bone structure, the support member having a pair of opposed vertically extending generally parallel surfaces;

holding the support member in place within the cavity by a plurality of lateral projections having horizontally extending upwardly facing surfaces extending in a transverse direction from said opposed surfaces into the filler material; and then closing the tissue flap over said cavity.

10. A method for inserting a dental implant into bone structure; comprising the steps of:

incising a tissue layer overlying the bone structure to provide a flap of tissue and expose a portion of said structure;

forming an elongate cavity in the exposed portion of the bone stucture;

applying a body of nontoxic filler material to substantially the entire interior surface of the cavity;

thereafter imbedding an elongate support member in the filler material in said cavity such that no portion of the support member contacts the bone structure, the support member having a pair of vertically extending generally parallel opposed surfaces;

holding the support member in place within the cavity by a plurality of planar lateral projections having horizontally extending upwardly facing surfaces extending in opposite directions from said opposed surfaces into the filler material; and closing the tissue flap over said cavity.

11. A method for inserting a dental implant into bone structure, comprising the steps of:

incising a tissue layer overlying the bone structure to provide a flap of tissue and expose a portion of said structure;

forming an elongate channel-shaped cavity in the exposed portion of the bone structure;

applying the body of nontoxic acrylic material to substantially the entire interior surface of the cavity;

thereafter embedding an elongate cobalt-chromium alloy support member in the acrylic material in said cavity such that no portion of the support member contracts the bone structure, the support member having a rectangular cross-section and a pair of opposed vertically extending generally parallel surfaces;

holding the support member in place within the cavity by means of a plurality of integrally formed relatively flat planar projections having horizontally extending upwardly facing surfces extending in a transverse direction from each of said opposed surfaces into the acrylice material; and then closing the tissue flap over said cavity.

* * * * *